United States Patent [19]

Berkelhammer et al.

[11] 4,105,780
[45] Aug. 8, 1978

[54] INSECTICIDAL AND ACARICIDAL M-PHENOXYBENZYL ESTERS OF 2,2-DIFLUORO-1,3-BENZODIOXOLE-5-(α-ALKYL)ACETIC ACIDS

[75] Inventors: Gerald Berkelhammer, Princeton, N.J.; Venkataramaran Kameswaran, Levittown, Pa.

[73] Assignee: American Cyanamid Company, Stamford, Conn.

[21] Appl. No.: 774,090

[22] Filed: Mar. 3, 1977

[51] Int. Cl.$^2$ .................... A01N 9/28; C07D 317/44
[52] U.S. Cl. ............................ 424/282; 260/340.5 R
[58] Field of Search .................... 260/340.5; 424/282

[56] References Cited

U.S. PATENT DOCUMENTS 3,872,105  3/1975  Grisar et al. ............... 260/340.5

OTHER PUBLICATIONS

Migrdichian, Organic Synthesis, vol. 2, p. 1395, Reinhold Publishing Corp., N.Y., 1957.

*Primary Examiner*—Ethel G. Love
*Attorney, Agent, or Firm*—H. G. Jackson

[57] ABSTRACT

The invention is novel m-phenoxybenzyl esters of 2,2-difluoro-1,3-benzodioxole-5-(α-alkyl)acetic acids, preparation thereof, and methods of use of the compounds for the control of insects and acarids.

16 Claims, No Drawings

INSECTICIDAL AND ACARICIDAL M-PHENOXYBENZYL ESTERS OF 2,2-DIFLUORO-1,3-BENZODIOXOLE-5-(α-ALKYL-)ACETIC ACIDS

The art discloses in South African patent application No. 73/4462, assigned to Sumitomo Chemical Co. Ltd. literally tens of thousands of phenylacetic acid esters including 3'-phenoxybenzyl-α-isopropyl-4-methoxyphenylacetate; 3'-phenoxybenzyl-α-isopropyl-3-methoxyphenylacetate; 3'-phenoxybenzyl-α-isopropyl-4-chlorophenylacetate; 3'-phenoxybenzyl-α-isopropyl-4-methylphenylacetate; 3'-phenoxybenzyl-α-isopropyl-3-chlorophenylacetate and 3'-phenoxybenzyl-α-isopropyl-4-fluorophenylacetate. They indicate that many of their compounds are effective pesticidal agents and useful for the control of a variety of insects and mites. The applicants do not, however, describe the m-phenoxybenzyl esters of 2,2-difluoro-1,3-benzodioxole-5-(α-alkyl) acetic acids which are the subject of the present invention; nor do they provide a synthesis applicable to the preparation of the compounds.

Surprisingly, we have found that the compounds of the present invention are not only effective insecticidal agents but are also highly effective ixodicidal agents. The compounds have a high margin of safety and can be used effectively to protect domestic, laboratory and farm animals from attack by insects and ticks. The compounds of this invention also exhibit residual ixodicidal and insecticidal activity, and are outstandingly effective for control of tobacco budworm and mosquitoes.

The invention is m-phenoxybenzyl esters of 2,2-difluoro-1,3-benzodioxole-5-(α-alkyl)acetic acids represented by the formula:

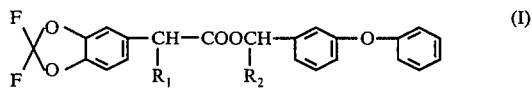

wherein $R_1$ is ethyl, n-propyl or i-propyl; $R_2$ is hydrogen or cyano, including the optical isomers thereof. The invention is also a method for controlling insects and acarina by contacting the insects and acarina, their habitat, breeding grounds and/or their food supply, with an insecticidally or acaricidally effective amount of a m-phenoxybenzyl ester of a 2,2-difluoro-1,3-benzodioxole-5-(α-alkyl)acetic acid. The invention includes a method for protecting agronomic crops, either growing or harvested, and homothermic animals from attack by insects and/or acarina by treating the crops and/or animals with an insecticidally or acaricidally effective amount of the above-identified m-phenoxybenzyl ester of a 2,2-difluoro-1,3-benzodioxole-5-(α-alkyl)acetic acid.

Advantageously, the m-phenoxybenzyl esters of the 1,3-benzodioxole-5-acetic acid can be prepared by reacting a 2,2-difluoro-1,3-benzodioxole-5-(α-alkyl)acetic acid halide (II), preferably chloride, with a m-phenoxybenzyl alcohol (III). The reaction is generally conducted in the presence of a solvent such as diethyl ether, benzene, or toluene, at a temperature between about 10° C and 30° C in the presence of an acid acceptor. Among the acid acceptors that can be employed are the tertiary organic amines, trimethylamine, triethylamine and pyridine. This reaction can be illustrated as follows:

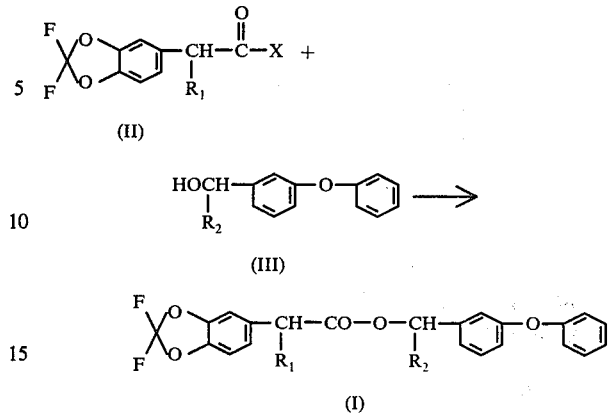

wherein $R_1$ is ethyl, n-propyl or i-propyl; $R_2$ is H or CN and X is halogen, preferably chlorine.

Preferred compounds within the generic formula I depicted above, are those wherein $R_1$ is isopropyl and $R_2$ is hydrogen or cyano.

With regard to the compounds of the present invention as depicted by formula I, it should also be understood that various optical isomers of the above-identified compounds do result from the preparations described.

For example, in the synthesis of formula I esters, wherein $R_2$ is hydrogen, a chiral center is present at $R_1$ and d and l isomeric pairs are formed. Also, α-cyano substitution at $R_2$ introduces an additional chiral center thus allowing for an additional d, l pair.

The 2,2-difluoro-1,3-benzodioxole-5-(α-alkyl)acetylhalide (II), can be prepared by using 5-methyl-1,3-benzodioxole (X) as a starting material. The process for the preparation involves 8 steps, the first of which is the halogenation of the 5-methyl-1,3-benzodioxole (X) with a halogenating agent, such as phosphorus pentachloride in the presence of an inert solvent such as toluene to yield the corresponding 2,2-dichloro-5-methyl-1,3-benzodioxole (IX). This compound (IX) is then converted to the corresponding 2,2-difluoro-5-methyl-1,3-benzodioxole (VIII) with antimony (III) fluoride in an inert solvent such as dioxane. Next, the thus obtained 2,2-difluoro-5-methyl-1,3-benzodioxole (VIII) is converted to the corresponding 5-halomethyl derivative by halogenation with bromine, chlorine, N-bromosuccinimide and the like. This reaction is preferably conducted in the presence of an inert solvent such as carbon tetrachloride, and a radical initiator such as light, benzoyl peroxide, or azo-bis-isobutyronitrile to yield 2,2-difluoro-5-halomethyl-1,3-benzodioxole (VII). The formula (VII) compound is then readily converted to the corresponding acetonitrile (VI) by reaction with sodium or potassium cyanide in the presence of dimethylsulfoxide (DMSO), ethanol or the like at an elevated temperature. This acetonitrile (VI) is readily alkylated when treated with an alkyl halide, alkyl sulfate, or alkyl sulfonate in the presence of a base and an inert solvent. Crown ethers have been found to be useful catalysts in this reaction. The α-alkylacetonitrile formed in the above reaction is depicted by formula (V) and hydrolysis of formula (V) α-alkylacetonitrile, using an alkali metal hydroxide in the presence of an alkylene glycol and water, yields the α-alkyl acetic acid shown as formula (IV). Treatment of the formula (IV) acid with thionyl chloride, thionyl bromide or the like, preferably in the presence of an aromatic solvent such as benzene or toluene, then yields 2,2-difluoro-1,3-benzodioxole-5-(α-alkyl)acetyl halide (II) which is then reacted with the m-phenoxybenzyl alcohol (III) to yield the desired m-phenoxybenzyl ester or α-cyano-m-phenoxybenzyl ester of 2,2-difluoro-1,3-benzodioxo-5-(α-alkyl)acetic acid (I).

These reactions are graphically illustrated in Flow Diagram I below.

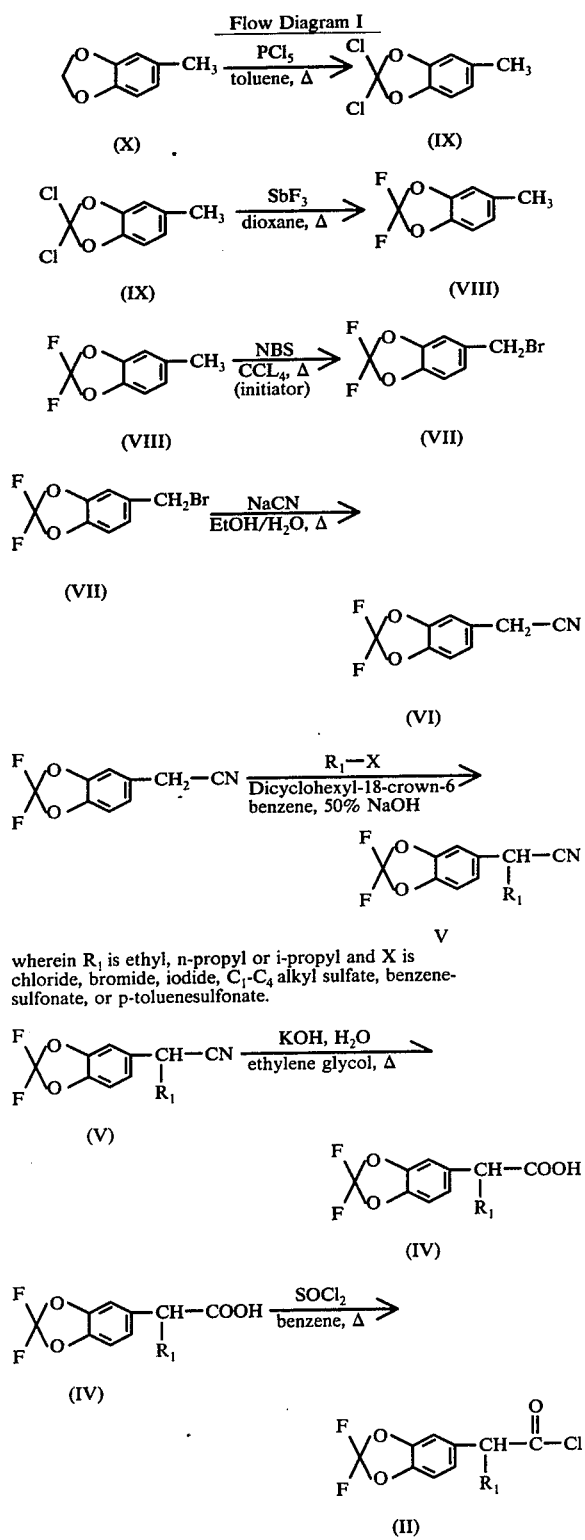

wherein $R_1$ is ethyl, n-propyl or i-propyl and X is chloride, bromide, iodide, $C_1$-$C_4$ alkyl sulfate, benzenesulfonate, or p-toluenesulfonate.

-continued
Flow Diagram I

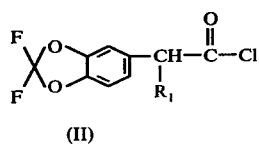

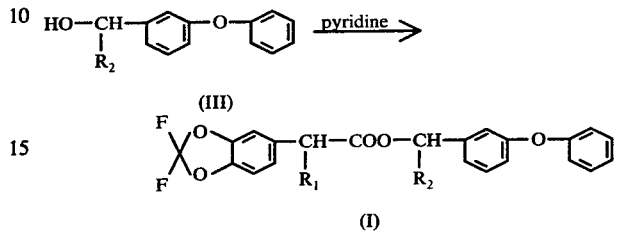

wherein $R_1$ is ethyl, n-propyl or i-propyl; $R_2$ is hydrogen or cyano.

With respect to the formation of the α-cyano-m-phenoxybenzyl ester products by the procedures illustrated in Flow Diagram I, it is not necessary to prepare the α-cyano-m-phenoxybenzyl alcohol precursor. It is equally or more satisfactory to allow a mixture of m-phenoxybenzaldehyde, an alkali cyanide such as sodium cyanide, and the appropriate α-substituted 1,3-benzodioxole-5-acetyl halide to react together in one step to form the final α-cyano ester.

The compounds of the invention are highly effective as contact and stomach poisons for ixodide ticks and for a wide variety of insects, particularly Dipterous, Lepidopterous, Coleopterous and Homopterous insects. The compounds are unusual among pyrethroids, in that they exhibit an extended residual insecticidal activity on plant tissue, they are effective in the soil, and are surprisingly effective for the control of ixodidae and the protection of animals against attack by insects and ixodidae when administered to the animals orally or parenterally or applied thereto as a topical insecticidal or acaricidal formulation. They do not require admixture with a stabilizing agent to achieve insecticidal and acaricidal compositions having stabilized effects; however, they may be used in combination with other biological chemicals, for example pyrethroid synergists such as piperonyl butoxide, sesamex or n-octyl sulfoxide of isosafrole. They may also be used in combination with conventional insecticides such as the phosphates, carbamates, formamidines, chlorinated hydrocarbons or halobenzoylureas. To achieve control of insects, including soil insects, which attack growing plants and/or harvested crops, including stored grain, the insecticidal compounds of this invention may be applied to the foliage of plants, the insect's habitat and/or the insect's food supply. Generally, the active compound is applied in the form of a dilute liquid spray; however, it may also be applied as an aerosol, a dust, a granular, or a wettable powder formulation.

Liquid sprays which are particularly useful are oil sprays and emulsifiable concentrates which can be further diluted for application. While they are, respectively, prepared as liquid concentrates; for convenience in handling and shipping, these formulations are usually dispersed in water at the site of their use and then applied as a dilute spray to the plant foliage, soil or surface of the area being treated.

A typical emulsifiable concentrate useful for protecting a variety of crops such as cereals, cole crops, cucurbits, corn, cotton, tobacco, soybeans, ornamentals, shrubs, and the like, may comprise about 20% by weight of the active agent; 4% by weight of an emulsifying agent, conventionally employed in the preparation of pyrethroid formulations; 4% by weight of a surfactant; 25% by weight of an organic solvent such as cyclohexanone; and about 47% by weight of a petroleum solvent having a minimum aromatic content of about 83 volume %.

For use as animal systemic insecticidal and acaricidal agents, the compounds of the invention can be administered to the animal host either orally or parenterally. When given orally, it may be in any convenient form designed for oral administration such as a bolus, capsule, tablet or as an oral drench. The active agent may also be incorporated in an edible animal feedstuff such as a nutritionally balanced diet containing from 0.0001% to 0.1% and preferably 0.001% to 0.05% by weight of feed of the active compound.

If desired, the systemic insecticidal and acaricidal agent may be introduced into the body of the animal by subcutaneous, intramuscular or intraperitoneal injection, such that it may be distributed through the animal's body by the action of the animal's circulatory system. In practice, the systemic agent may be dissolved or dispersed in a pharmaceutically acceptable carrier such as water, propylene glycol, vegetable oil, glycerol formal or the like, for administration.

Advantageously, the systemic agents have a good margin of safety and are effective for protecting a variety of animals, particularly livestock and domestic animals such as cattle, sheep, horses, dogs, cats, and the like, from attack by fleas, mosquitoes, flies, ticks, and the like.

Among the compounds of this invention which are useful as insecticidal and acaricidal agents are:
m-Phenoxybenzyl ester of 2,2-difluoro-1,3-benzodioxole-5-(α-ethyl)acetic acid;
α-Cyano-m-phenoxybenzyl ester of 2,2-difluoro-1,3-benzodioxole-5-(α-ethyl)acetic acid;
m-Phenoxybenzyl ester of 2,2-difluoro-1,3-benzodioxole-5-(α-propyl)acetic acid:
α-Cyano-m-phenoxybenzyl ester of 2,2-difluoro-1,3-benzodioxole-5-(α-propyl)acetic acid;
m-Phenoxybenzyl ester of 2,2-difluoro-1,3-benzodioxole-5-(α-i-propyl)acetic acid;
α-Cyano-m-phenoxybenzyl ester of 2,2-difluoro-1,3-benzodioxole (α-i-propyl)acetic acid The invention is further described by the examples set forth below which are not to be construed as limiting the invention.

EXAMPLE 1

Preparation of 2,2-Dichloro-5-methyl-1,3-benzodioxole

A slurry of 5-methyl-1,3-benzodioxole (52.6 g, 0.387 mole) and phosphorus pentachloride (102.4 g) in toluene is stirred and heated at 70° C for 2 hours. The temperature is then raised to 90° C over 30 minutes and held for 4 hours. Phosphorus trichloride is distilled off at atmospheric pressure. Vacuum distillation yields 73.4 g of product 2,2-dichloro-5-methyl-1,3-benzodioxole (yield: 92%); $n_D^{24}$ 1.5325; b.p. 78°–82° C (at 0.4 mm); nmr (CDCl$_3$) δ 2.28 (S 3H), 6.8 (m 3H).

EXAMPLE 2

Preparation of 2,2-Difluoro-5-methyl-1,3-benzodioxole

Dry dioxane (172 ml) and antimony (III) fluoride (56.2 g, 0.314 mole) are mixed and a part of the solvent (57 m) is distilled off. The mixture is cooled to room temperature and a solution of 2,2-dichloro-5-methyl-1,3-benzodioxole (65.0 g, 0.317 mole) in dioxane (68 ml) is added dropwise over 30 minutes. During this time the temperature of the reaction mixture rises to 42° C. The solution is refluxed for 7 hours, poured into a mixture of concentrated hydrochloric acid (100 ml) and water (100 ml), extracted with ether (3×100 ml). The ether extracts are combined, washed with water, dried over sodium sulfate and evaporated. The residual oil is distilled under reduced pressure (obtained by using a water-aspirator) to yield 29.3 g of product 2,2-difluoro-5-methyl-1,3-benzodixole (yield 53%; nmr (CDCl$_3$) δ 2.28 (S, 3H), 6.8–6.8 (m, 3H).

EXAMPLE 3

Preparation of 2,2-Difluoro-5-bromomethyl-1,3-benzodioxole

A mixture of 2,2-difluoro-5-methyl-1,3-benzodioxole (29.0 g, 0.169 mole), N-bromosuccinimide (30.1 g, 0.169 mole), benzoyl peroxide (0.5 g) and carbon tetrachloride (50 ml) is refluxed for 2.5 hours. Carbon tetrachloride (50 ml) is then added to the hot reaction mixture and the solids are filtered off. The filtrate and washings are evaporated to yield 41.0 g of product as a brown oil; nmr (CCl$_4$) δ 4.38 (S, 2H), 6.8–7.4 (m, 3H). The product is used without purification in the next step.

EXAMPLE 4

Preparation of 2,2-Difluoro-1,3-benzodioxole-5-acetonitrile

To a solution of 2,2-difluoro-5-bromomethyl-1,3-benzodioxole (41.0 g) in absolute alcohol (160 ml) at 60°–70° C a hot solution of potassium cyanide (22.1 g, 0.34 mole) in water (30 ml) is added. There is a slight exotherm and within 5 minutes potassium bromide separates out of the reaction mixture. The reaction mixture is refluxed for 1.5 hours, cooled and added to ice-water. The mixture is extracted with ether (3×100 ml), the combined extracts are washed with water (2×50 ml), dried over sodium sulfate and evaporated to afford a dark oil. Vacuum distillation yields 21.2 g of product (64% yield); b.p. 64°–67° C (at 0.03 mm); i.r. (neat) 2255 cm$^{-1}$; nmr (CCl$_4$) δ 3.68 (S, 2H), 7.00 (S, 3H).

EXAMPLE 5

Preparation of 2,2-Difluoro-1,3-benzodioxole-5-(α-isopropyl)-acetonitrile

A solution of 50% sodium hydroxide (25 ml) is added to a solution of 2,2-difluoro-1,3-benzodioxole-5-acetonitrile (18.0 g, 0.0913 mole), 2-bromopropane (11.23 g, 0.0913 mole) and dicyclohexyl-18-crown-6* (1.7 g, 5 mole percent) in benzene (10 ml). The reaction temperature rises to 44°–45° C over 15 minutes. The reaction mixture is then stirred at room temperature for 5 hours. More 2-bromopropane (2.8 g, 25 mole percent excess) is added and the reaction mixture stirred for 3 days. The organic layer is separated, the aqueous layer is extracted with ether (2×50 ml) and the extracts are combined with the organic layer. The combined organic solution is washed with water (2×50 ml), dilute hydrochloric acid (50 ml), water (2×50 ml), is dried over sodium sulfate and evaporated to afford an oil. Vacuum distillation yields 16.35 g of product (75% yield); b.p. 67°–69° C (at 0.03 mm); i.r. (neat) 2250 cm$^{-1}$; nmr (CCl$_4$) δ 1.05 and 1.08 (each d, J=7Hz, 6H), 2.1 (m, 1H), 3.68 (d, J=7Hz, 1H), 7.05 (S, 3H).

*The structure of dicyclohexyl-18-crown-6 is:

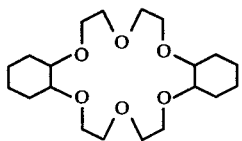

By the above procedure, but substituting 1-iodopropane or iodoethane for 2-bromopropane, 2,2difluoro-1,3-benzodioxole-5-(α-propyl)acetonitrile and 2,2-difluoro-1,3-benzodioxole-5-(α-ethyl)acetonitrile are prepared, respectively.

EXAMPLE 6

Preparation of
2,2-Difluoro-1,3-benzodioxole-5-(α-isopropyl)-acetic acid

A mixture of 2,2-difluoro-1,3-benzodioxole-5-(α-isopropyl)acetonitrile (13.5 g), potassium hydroxide pellets (20.0 g) in ethylene glycol (100 ml) and water (20 ml) is heated at 140° C with stirring for 14 hours. After cooling, the reaction mixture is poured into water and extracted with ether (2×50 ml). The aqueous portion is cautiously acidified with hydrochloric acid and extracted with ether (3×50 ml). The combined extracts are washed with water (2×50 ml), dried over sodium sulfate and evaporated to dryness. Recrystallization of the solid residue from heptane affords 9.4 g of product (64% yield); m.p. 98°–101° C, i.r. (Nujol mull) 1700 cm$^{-1}$; nmr (CDCl$_3$) δ 0.75 (d, J=8Hz, 3H), 1.10 (d, J=8Hz, 3H), 2.3 (m, 1H), 3.16 (d, J=10Hz, 1H), 7.0–7.2 (m, 3H).

By the above procedure, but substituting 2,2-difluoro-1,3-benzodioxole-5-(α-propyl)acetonitrile and 2,2-difluoro-1,3-benzodioxole-5-(α-ethyl)acetonitrile for 2,2-difluoro-1,3-benzodioxole-5-(α-isopropyl)acetonitrile, 2,2-defluoro-1,3-benzodioxole-5-(propyl)acetic acid and 2,2-difluoro-1,3-benzodioxole-5-(ethyl)acetic acid are prepared, respectively.

EXAMPLE 7

Preparation of
2,2-Difluoro-1,3-benzodioxole-5-(α-isopropyl)-acetyl chloride

A solution of 2,2-difluoro-1,3-benzodioxole-5-(α-isopropyl)acetic acid (5.16 g, 0.02 mole) and thionyl chloride (2 ml) in benzene (10 ml) is refluxed for 4 hours. Evaporation of the solvent and excess thionyl chloride affords the title product which is used without further purification in the subsequent step.

By the above procedure, but substituting 2,2-difluoro-1,3-benzodioxole-5-(α-propyl)acetic acid and 2,2-difluoro-1,3-benzodioxole-5-(α-propyl)acetic acid or 2,2-difluoro-1,3-benzodioxole-5-(α-ethyl)acetic acid for 2,2-difluoro-1,3-benzodioxole-5-(α-isopropyl)acetic acid, 2,2-difluoro-1,3-dioxole-5-(α-isopropyl)acetic acid, 2,2-difluoro-1,3-dioxole-5-(α-propyl)acetyl chloride and 2,2difluoro-1,3-benzodioxole-5-(α-ethyl)acetyl chloride are prepared, respectively.

EXAMPLE 8

Preparation of α-Cyano-m-phenoxybenzyl ester of
2,2-difluoro-1,3-benzodioxole-5-(α-isopropyl)acetic acid A solution of 2,2-difluoro-1,3-benzodioxole-5-(α-isopropyl)acetyl chloride (0.01 mole) in ether (10 ml) is added to a solution of α-cyano-m-phenoxybenzyl alcohol 2.03 g, 90 mole percent) and pyridine (0.8 g) in ether (25 ml) at room temperature. The reaction mixture is stirred overnight at room temperature. The solids are filtered off, and the filtrate and washings are evaporated to yield an oil. The oil is purified by dry column chromatography on silica gel using 1:1 methylene chloride-hexane as eluent to afford 3.40 g of title product (73% yield; nmr (CDCl$_3$) 0.6–1.1 (set of d, 6H), 2.3 (m, 1H), 3.2 (d, J=10Hz, 1H), 6.30 and 6.35 (S, 1H), 6.8–7.5 (m, 12H).

By the above procedure, but substituting 2,2-difluoro-1,3-benzodioxole-5-(α-propyl)acetyl chloride and 2,2-difluoro-1,3-benzodioxole-5-(α-ethyl)acetyl chloride the α-cyano-m-phenoxybenzyl esters of 2,2-difluoro-1,3-benzodioxole-5-(α-propyl)acetic acid and 2,2-difluoro-1,3-benzodioxole are prepared, respectively.

EXAMPLE 9

Preparation of m-Phenoxybenzyl ester of
2,2-difluoro-1,3-benzodioxole-5-(α-isopropyl)acetic acid The title compound is prepared by the procedure of Example 8 by substituting m-phenoxybenzyl alcohol for α-cyano-m-phenoxybenzyl alcohol; nmr (CDCl$_3$) δ 0.65 and 0.95 (each d, J=8H$_2$, 6H), 2.3 (m, 1H), 3.15 (d, J=10Hz, 1H), 5.02 (Collapsed AB pattern, 2H) 6.7–7.4 (m, 12H).

By the above procedure, but substituting 2,2-difluoro-1,3-benzodioxole-5-(α-propyl)acetyl chloride and 2,2-difluoro-1,3-benzodioxole-5-(α-ethyl)acetyl chloride, the m-phenoxybenzyl esters of 2,2-difluoro-1,3-benzodioxole-5-(α-propyl)acetic acid and 2,2-difluoro-1,3-benzodioxole-5-(α-ethyl)acetic acid are prepared, respectively.

EXAMPLE 10

Residual insecticidal activity obtained with foliar treatment of cotton plants

Young cotton plants with at least two expanded true leaves growing in 10 cm plastic pots were dipped, usually one leaf at a time, in a 65% acetone-35% water solution of test compound with agitation for 3 seconds. The concentration of each compound in the solutions was 30 ppm, 100 ppm, 300 ppm or 900 ppm of active ingredient.

After the leaves had dried, two leaves from each of two plants were excised and placed in petri dishes (90 mm ×0 10 mm) on moist filter paper (9 cm Whatman No. 1) Five third instar tobacco budworm larvae were placed on each leaf and the petri dish capped. The infested dishes were then placed in the holding room with continuous light, ambient temperature of 80° F and 50% r.h. Larval counts were made after 72 hours.

The remaining plants were placed under high intensity lights in the greenhouse adjusted to provide 14 hours of light per day. Leaf samples were assayed with third instar tobacco budworm larvae after 3, 7, 10 and 14 days exposure in the greenhouse.

The data obtained are summarized in Table I. The well-known pyrethroid permethrin is included as a reference standard.

employed as test insect species. Procedures employed are as follows:

Tobacco Budworm *Heliothis virescens* (Fabricius).

First Instar

Table I

Residual Insecticidal Activity of Test Compounds on Cotton Plants Using Third-Instar Tobacco Budworm Larvae for Bioassay

| Compound | Rate ppm | Days Residual Activity | | | | | | | | | |
|---|---|---|---|---|---|---|---|---|---|---|---|
| | | 0 | | 3 | | 7 | | 10 | | 14 | |
| | | 1* | 2** | 1 | 2 | 1 | 2 | 1 | 2 | 1 | 2 |
| F₂C(O)₂-C₆H₃-CH(CH(CH₃)₃)-COOCH₂-C₆H₄-O-C₆H₅ | 30 | 45 | 1.6 | 0 | 16.3 | 10 | 37.5 | 10 | 20.3 | 10 | 56.3 |
| | 100 | 90 | 0 | 55 | 1.1 | 55 | 1.3 | 65 | 0.1 | 10 | 8.8 |
| | 300 | 95 | 0 | 90 | 0 | 100 | 0 | 90 | 0 | 95 | 0 |
| | 900 | 100 | 0 | 100 | 0 | 100 | 0 | 100 | 0 | 100 | 0 |
| F₂C(O)₂-C₆H₃-CH(CH(CH₃)₂)-COOCH(CN)-C₆H₄-O-C₆H₅ | 100 | 85 | 0 | 85 | 0 | 100 | 0 | 65 | 0.03 | 90 | 0.03 |
| | 300 | 100 | 0 | 100 | 0 | 90 | 0 | 90 | 0 | 100 | 0 |
| | 900 | 100 | 0 | 100 | 0 | 100 | 0 | 95 | 0 | 100 | 0 |
| Cl₂C=CH-(CH₃)₂C-COOCH₂-C₆H₄-O-C₆H₅ Permethrin | 30 | 65 | 0.3 | 30 | 11.3 | 15 | 12.5 | 40 | 4.3 | 5 | 0 |
| | 100 | 85 | 0 | 85 | .03 | 70 | .53 | 65 | 0.6 | 25 | 14 |
| | 300 | 100 | 0 | 100 | 0 | 100 | 0 | 95 | 0 | 80 | 77 |
| | 900 | 100 | 0 | 100 | 0 | 100 | 0 | 90 | 0 | 100 | 100 |
| Control | — | 0 | 100 | 0 | 96.5 | 5 | 90 | 0 | 73.8 | 13 | 80 |

1* = Average % Mortality 2OTBW/Point
2** = Average % Feeding Damage

EXAMPLE 11

The effectiveness of the compounds of the invention for controlling adult *Boophilus microplus* ticks is determined in the following tests wherein test compound is dissolved in 10% acetone-90% water mixture in sufficient amounts to give solutions containing 125, 62.5, 31.2, 15.6 or 7.3 ppm of test compound.

Adult engorged female ticks are then dipped in the test solutions for 3 seconds and placed in individual containers and held for 48 hours in a room maintained at 80° F and 50% r.h. At the end of the holding period the ticks are examined and egg deposits counted. Engorged females that do not deposit eggs are considered dead. Data obtained are reported below in Table II.

A cotton plant with two true leaves expanded is dipped for 3 seconds with agitation in a test solution (35% water/65% acetone) containing 300, 100 or 10 ppm of test compound. Each leaf is placed in a cup with a wick and a piece of cheesecloth infested with 50-100 newly hatched larvae is added before covering the cup with a lid. After 3 days at 80° F, 50% r.h., the cups are examined and the kill of newly hatched larvae noted. Data obtained are reported as percent kill in Table III.

Bean Aphid, *Aphis fabae* (Scopoli).

Five cm fiber pots, each containing a nasturtium plant 2 inches high and infested with 100 to 150 aphids 2 days earlier are placed on a 4 rpm turntable and sprayed with a 35% water/65% acetone solution containing 100, 10,

Table II

| Compound | Percent Adult Tick Mortality at Concentration (ppm) | | | | |
|---|---|---|---|---|---|
| | 125 | 62.5 | 31.2 | 15.6 | 7.3 |
| F₂C(O)₂-C₆H₃-CH(CH(CH₃)₃)-COOCH₂-C₆H₄-O-C₆H₅ | 80.5 | 52.6 | 30.8 | 20.3 | 3.5 |
| F₂C(O)₂-C₆H₃-CH(CH(CH₃)₃)-COOCH(CN)-C₆H₄-O-C₆H₅ | 98.3 | 99.7 | 88.4 | 85.8 | 80.2 |

EXAMPLE 12

Insecticidal Activity

The insecticidal activity of the compounds of this invention is demonstrated in the following tests, wherein Tobacco budworm, *Heliothis virescens* (Fabricius); Western Potato Leafhopper, *Empoasca abrupta* DeLong and Bean Aphid, *Aphis fabae* (Scopoli), are 1.0 and 0.1 ppm of test compound for 2 revolutions using a DeVilbiss Atomizer and 20 psi air pressure. The spray tip is held about 15 cm from the plant and the spray directed so as to give complete coverage of the aphids and the plants. The sprayed plants are laid on their sides on white enamel trays. Mortality estimates are made after 1 day at 70° F, 50% r.h.

Data are reported as percent mortality determined at the rate indicated (Table III).

Western Potato Leafhopper, *Empoasca abrupta* DeLong

A Sieve lima bean plant with the primary leaf expanded to 3 to 4 inches is dipped into 35% water/65% acetone solution containing 100, 10 or 1 ppm of test compound. The dipped plant is placed in the hood to dry and then a 2.5 cm piece of the tip of one leaf is cut off and placed in a 4-inch petri dish with a moist filter paper in the bottom. From 3 to 10 second-instar nymphs are placed in the dish and the dish is then covered. Mortality counts are made after holding the thus-prepared dish for 2 days at 80° F and 50 r.h. Data obtained are reported in Table III. In these tests permethrin is used as a standard or check.

are made. Percent mortality records are presented in Table IV.

Mexican Bean Beetle — *Epilachna varivestis* Mulsant

Sieva lima bean plants (2 per pot) with primary leaves 7.5 to 10 cm long, are dipped in the 300, 100, 10 or 1 ppm test solution and set in the hood to dry. One leaf is removed from a plant and placed in a 10 cm petri dish containing a moist filter paper on the bottom and 10 last-instar larvae (13 days from hatching). The day after treatment, another leaf is removed from the plant and fed to the larvae after removing the remains of the original leaf. Two days after treatment, the third leaf is fed to the larvae, this usually being the last needed. The fourth leaf is used on the third day after treatment if the

Table III
Insecticidal Evaluation

| | % Mortality | | | | | | | |
|---|---|---|---|---|---|---|---|---|
| | Tobacco Budworm Larvae, 1st Instar ppm | | | Leaf Hopper ppm | | Aphids ppm | | |
| Compound | 300 | 100 | 10 | 100 | 10 | 100 | 10 | 1.0 |
| 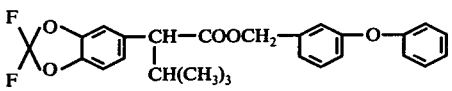 | 100 | 100 | 0 | 0 | | 100 | 100 | 20 |
| 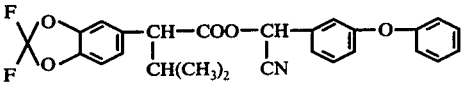 | 100 | 100 | 90 | 100 | 90 | 100 | 100 | 90 |
| 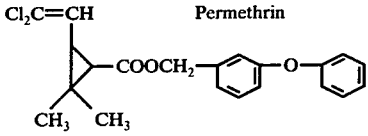 Permethrin | 100 | 100 | 50 | 100 | 0 | 100 | 100 | 100 |

EXAMPLE 13
Insecticidal Activity

The insecticidal activity of the compounds of the present invention, is further demonstrated by the following tests.

The procedures employed for evaluation against mosquito larvae, Mexican Bean Beetles and Soutern Armyworms are as follows.

Malaria Mosquito — *Anapheles quadrimaculatus* Say

1 Milliliter of a 35% water/65% acetone solution containing 300 ppm of test compound is pipetted in a 400 ml beaker containing 250 ml of deionized water and stirred with the pipette, giving a concentration of 1.2 ppm. Aliquots of this solution are taken and further diluted to .4, .04, and .004 ppm. A wax paper ring 0.6 cm wide to fit inside the beaker is floated on the surface of the test solution to keep the eggs from floating up the meniscus curve and drying out on the side of the glass. A spoon made of screen is used to scoop up and transfer about 100 eggs (0–24 hours old) into the test beaker. After 2 days at 80° F, 50% r.h., observations of hatching larvae have not finished feeding. The test is now set aside and held until adults have emerged, usually in about 9 days after treatment began. After emergence is complete, each dish is examined for dead larvae, pupae or adults; deformed pupae or adults; larval-pupal intermediates or pupal-adult intermediates; or any other interference with normal molting, transformation and emergence of pupae or adults.

Data obtained are reported in Table IV.

Southern Armyworm — *Spodoptera eridania* (Cramer)

Methods:

Sieva lima bean plants, with two expanded 7.5 to 10 cm primary leaves, are dipped 3 seconds with agitation in the treatment solutions and then set in a hood to dry. After the leaves are dry they are excised and each excised leaf is placed in a 10 cm petri dish containing a piece of moist filter paper and 10 third-instar southern armyworm larvae approximately 1 cm long. The petri dishes are covered and placed in a holding room for 2 days at a temperature of 80° F and 50% relative humidity.

Mortality counts are made after 2 days. Results obtained are presented in Table IV.

Table IV

| | Insecticidal Evaluation | | | | | | | | |
|---|---|---|---|---|---|---|---|---|---|
| | % Mortality | | | | | | | | |
| | Mosquito Larvae ppm | | | Southern Armyworm ppm | | | Mexican Bean Beetle ppm | | |
| Compound | 1.2 | .4 | .04 | 1000 | 100 | 10 | 300 | 100 | 10 |
| 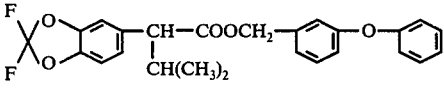 | 90 | 90 | 90 | 100 | 100 | 60 | 100 | 100 | 80 |
| 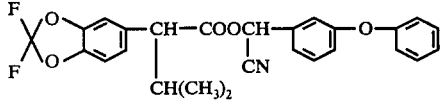 | 100 | 100 | 100 | 100 | 100 | 100 | 100 | 100 | 100 |
| 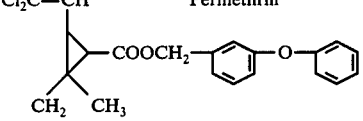 Permethrin | 100 | 100 | 100 | 100 | 100 | 100 | 100 | 90 | 0 |

EXAMPLE 14

Insecticidal Activity

Two-Spotted Spider Mite — *Tetranychus urticae* (Koch)

Sieve lima bean plants, with primary leaves three 7.5 to 10 cm long, are infested with about 100 adult phosphate resistant mites per leaf 4 hours before use in this test, in order to allow egg-laying before treatment. The infested plants are dipped for 3 seconds with agitation into the 300, 100 or 10 ppm solution, and the plants set in the hood to dry. After 2 days at 80° F, the adult mite mortality is estimated on one leaf under a 10X stereoscopic microscope. The other leaf is left on the plant an additional 5 days and then examined at 10X power to estimate the kill of eggs and of newly-hatched nymphs, giving a measure of ovicidal and residual action, respectively. Test results are provided in Table V.

Tobacco Budworm — *Heliothis virescens* (Fabricus)

Third Instar

Three cotton plants with just expanded cotyledons are dipped in 1000 or 100 ppm solution and placed in the hood to dry. When dry, each cotyledon is cut in half, and 10 leaf sections are each placed in a 28 g plastic medicine cup containing a 1.25 cm dental wick saturated with water and one third-instar budworm larva is added. The cup is capped and held for 3 days at 80° F 50% r.h., after which mortality counts are made. Test results provided in Table V.

Cabbage Looper — *Trichoplusia ni* (Hubner) — Third Instar

A true leaf on a cotton plant is dipped into the test solution containing 1000 or 100 of test compound, agitated for 3 seconds, and removed to dry in an exhaust hood. When dry, the leaf is placed in a 9.0 cm petri dish with moist filter paper on the bottom. Ten third-instar larvae are added and the lid placed on the dish. Mortality counts are made after 3 days at 80° F and 50 ± 10% r.h.

Data obtained are reported in Table V below.

Table V

| | % Mortality | | | | | | |
|---|---|---|---|---|---|---|---|
| | Phosphate Resistant mites ppm | | | 3rd Instar Tobacco Budworm ppm | | 3rd Instar Cabbage Looper ppm | |
| Compound | 300 | 100 | 10 | 1000 | 100 | 1000 | 10 |
| 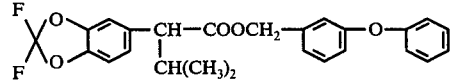 | 100 | 0 | — | 80 | 40 | 100 | 60 |
| 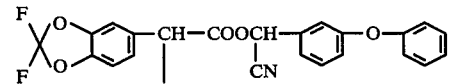 | 100 | 100 | 0 | 100 | 100 | 100 | 100 |
| 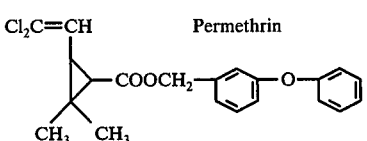 Permethrin | 100 | 50 | 0 | 100 | 100 | 100 | 100 |

EXAMPLE 15

Determination of the Efficacy of the test compounds against adult mosquitoes *Anopheles quadrimaculatus* Say The compounds to be evaluated were prepared in acetone at the desired concentration in ppm. To produce an aerosol application the insecticide solutions were pipetted (0.15 ml) into the top of a nozzle and siphoned through the atomizer nozzle. The atomized droplets are carried by an air stream (4 miles/hour) to the caged mosquitoes (25 adult females/cage) for a 4-5 seconds exposure. The mosquitoes were then anesthetized (3-4 seconds) with $CO_2$ and transferred to holding cages. The holding cages of treated mosquitoes were placed in a holding room at 85° ± 1° F and 46 ± 2% relative humidity. Mortality counts were made after 24 hours.

Data obtained are reported in Table IV below where it can be seen that the compounds of the invention are more effective than the art compound for controlling adult *Anopheles quadrimaculatus*.

Table VI
Efficacy of Test Compounds Against
*Anopheles quadrimaculatus*
Adult Females

| Compound | Concentration (ppm) | % Mortality |
|---|---|---|
| (structure 1) | 1 | 20 |
|  | 10 | 90 |
| (structure 2) | 1 | 30 |
|  | 10 | 100 |
| Permethrin 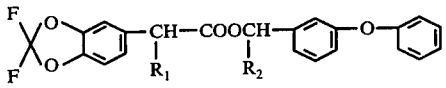 | 1 | 0 |
|  | 10 | 50 |

We claim:

1. A compound having the formula:

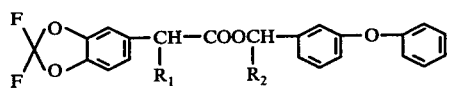

wherein $R_1$ is ethyl, n-propyl or i-propyl and $R_2$ is hydrogen or cyano.

2. A compound according to claim 1, wherein $R_1$ is ethyl, n-propyl or i-propyl and $R_2$ is hydrogen.

3. A compound according to claim 1, wherein $R_1$ is ethyl, n-propyl or i-propyl and $R_2$ is cyano.

4. A compound according to claim 2, the m-phenoxybenzyl ester of 2,2-difluoro-1,3-benzodioxole-5-(α-ethyl)acetic acid.

5. A compound according to claim 2, the m-phenoxybenzyl ester of 2,2-difluoro-1,3-benzodioxole-5-(α-propyl)acetic acid.

6. A compound according to claim 2, the m-phenoxybenzyl ester of 2,2-difluoro-1,3-benzodioxole-5-(α-i-propyl)acetic acid.

7. A compound according to claim 3, the α-cyano-m-phenoxybenzyl ester of 2,2-difluoro-1,3-benzodioxole-5-(α-ethyl)acetic acid.

8. A compound according to claim 3, the α-cyano-m-phenoxybenzyl ester of 2,2-difluoro-1,3-benzodioxole-5-(α-i-propyl)acetic acid.

9. A method for controlling insects and acarina, comprising contacting the insects and acarina, their habitat, breeding grounds or feed, with an insecticidally or acaricidally effective amount of a m-phenoxybenzyl ester of a 2,2-difluoro-1,3-benzodioxole-5-(α-alkyl)acetic acid having the structure:

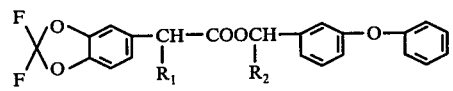

wherein $R_1$ is ethyl, n-propyl or i-propyl and $R_2$ is hydrogen or cyano.

10. A method according to claim 9, wherein the compound is the m-phenoxybenzyl ester of 2,2-difluoro-1,3-benzodioxole-5-(α-isopropyl)acetic acid.

11. A method according to claim 9, wherein the compound is the α-cyano-m-phenoxybenzyl ester of 2,2-difluoro-1,3-benzodioxole-5-(α-isopropyl)acetic acid.

12. The method for the systemic control of insects and acarina that feed on the body fluids of livestock and domestic animals comprising orally or parenterally administering to the animal host a systemically insecticidal or acaricidal effective amount of a compound having the formula:

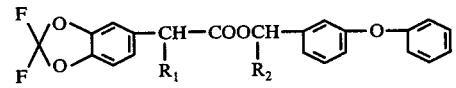

wherein $R_1$ is ethyl, n-propyl or i-propyl and $R_2$ is hydrogen or cyano.

13. A method according to claim 12, wherein the compound is orally administered to the host animal.

14. A method according to claim 12, wherein the compound is parenterally administered to the host animal.

15. An insecticidal/acaricidal composition comprising
an insecticidally or acaricidally effective amount of a compound having the formula wherein $R_1$ is ethyl, n-propyl or i-propyl and $R_2$ is hydrogen or cyano;
an emulsifying agent,
a surfactant and
solvent.

* * * * *